United States Patent
Spier

(10) Patent No.: US 10,603,217 B2
(45) Date of Patent: Mar. 31, 2020

(54) SURGICAL ROBOTIC INSTRUMENT SHIELD

(71) Applicant: Laurence Spier, Roslyn, NY (US)

(72) Inventor: Laurence Spier, Roslyn, NY (US)

( * ) Notice: Subject to any disclaimer, the term of this patent is extended or adjusted under 35 U.S.C. 154(b) by 527 days.

(21) Appl. No.: 14/755,896

(22) Filed: Jun. 30, 2015

(65) Prior Publication Data

US 2016/0000606 A1    Jan. 7, 2016

Related U.S. Application Data

(60) Provisional application No. 62/019,709, filed on Jul. 1, 2014.

(51) Int. Cl.
| | | |
|---|---|---|
| *A61F 9/02* | (2006.01) | |
| *A61B 90/00* | (2016.01) | |
| *A61B 34/37* | (2016.01) | |

(52) U.S. Cl.
CPC .............. *A61F 9/029* (2013.01); *A61B 34/37* (2016.02); *A61B 90/05* (2016.02)

(58) Field of Classification Search
CPC .. A61F 9/029; A61F 9/026; A61F 9/02; A61F 9/04; A61F 5/3707; A61B 34/37; A61B 90/05; A61B 46/10; A61B 90/20; A61B 2017/00902; A61B 19/081; A61B 90/50; G02B 21/0012; G02B 27/0006; G02B 21/24; G02B 23/16; G02B 7/02; G02B 25/001; G02B 7/001; G02B 1/11; G02B 21/02; G02B 21/16; G02B 21/26; A41D 13/11
See application file for complete search history.

(56) References Cited

U.S. PATENT DOCUMENTS

| | | | | |
|---|---|---|---|---|
| 3,698,791 A | * | 10/1972 | Walchle | G02B 7/001 |
| | | | | 359/510 |
| 4,850,049 A | | 7/1989 | Landis et al. | |
| 5,099,525 A | | 3/1992 | Millauro | |
| 5,424,787 A | | 6/1995 | Zegarelli | |
| 6,024,454 A | * | 2/2000 | Horan | G02B 21/0012 |
| | | | | 206/316.1 |
| 6,116,741 A | * | 9/2000 | Paschal | G02B 21/0012 |
| | | | | 206/316.1 |
| 8,206,406 B2 | | 6/2012 | Orban, III | |
| 2010/0225209 A1 | | 9/2010 | Goldberg et al. | |
| 2011/0261166 A1 | | 10/2011 | Olazaran | |
| 2014/0275935 A1 | * | 9/2014 | Walsh | A61F 9/026 |
| | | | | 600/398 |

(Continued)

FOREIGN PATENT DOCUMENTS

AU    634496 B2    5/1990

OTHER PUBLICATIONS

International Search Report and Written Opinion dated Oct. 22, 2015 in International Patent Application No. PCT/US2015/038594.

(Continued)

*Primary Examiner* — Ophelia A Hawthorne
(74) *Attorney, Agent, or Firm* — Kramer Levin Naftalis & Frankel LLP

(57) ABSTRACT

The present invention provides, in various embodiments, an instrument shield for a robotic surgical system comprising eye shield(s) and/or a face shield mounted on the instrument to protect surgeons from contaminants.

6 Claims, 8 Drawing Sheets

(56) References Cited

U.S. PATENT DOCUMENTS

2015/0181951 A1   7/2015  Kaforey
2015/0245675 A1*  9/2015  Chinquee ............ A41D 13/1184
                                                        2/424

OTHER PUBLICATIONS

Partial European Search Report Application No. 15815187.8, dated Dec. 15, 2017.
Extended European Search Report Application No. 15815187.8, dated Mar. 20, 2018.

* cited by examiner

SURGICAL ROBOTIC INSTRUMENT SHIELD

RELATED APPLICATIONS

This application claims the benefit of, and priority to, U.S. Provisional Application No. 62/019,709, filed Jul. 1, 2014, entitled "Surgical Robotic Instrument Shield," which is incorporated herein by reference in its entirety.

BACKGROUND

Traditional surgeries are often open procedures, which require long incisions through which the surgeon operates. Increasingly, minimally invasive procedures are being used in place of traditional surgeries for a range of operations, including General Surgery, Gynecologic Surgery, Head and Neck Surgery, Urologic Surgery, Colorectal Surgery, Bariatric Surgery, Cardiac Surgery, Thoracic Surgery and others. Advantages of minimally invasive procedures as compared to traditional surgeries include, but are not limited to, smaller incisions, reduced blood loss, improved wound healing, and shorter hospital stays.

Minimally invasive surgeries can be performed using robotic surgical systems (e.g., the da Vinci® surgical system from Intuitive Surgical, Inc. and others by Medtronic, Ethicon, etc.), in which specialized robotic surgical instruments are operated by the surgeon from a computer console. Such systems typically comprise a patient cart (FIG. 1B), which is positioned adjacent to the patient and contains the arms of the robot with surgical instruments attached thereto (these instruments are placed into the patient's body through trocars that are clamped to the robot arms), and a surgeon console (FIGS. 1A and 1C), which is located away from the patient, from which the surgical instruments on the patient cart are controlled by the surgeon under 3D high definition vision.

SUMMARY

The present invention provides, in various embodiments, an instrument shield for a robotic surgical system, which protects part or all of the surgeon's face from contaminants on the faceplate or the optical portion of the surgeon console.

In some embodiments, the instrument shield comprises an eye shield configured to be removably attached to an eyepiece of the surgeon console, said eyepiece having a glass portion and a raised rim, and said eye shield comprising a transparent lens covering the glass portion of the eyepiece. In some embodiments, the transparent lens of the eye shield comprises clear plastic.

In some embodiments, the eye shield comprises a concave rim molded to fit onto the rim of the eyepiece. In some embodiments, the eye shield is removably attached to the eyepiece with adhesive.

In some embodiments, the instrument shield comprises two eye shields. In some embodiments, the instrument shield further comprises a face shield. In some embodiments, the face shield is attached to the eye shields. In other embodiments, the face shield is removably attached to the console separate from the eye shields. In some embodiments, the face shield is removably attached to a faceplate of the console with adhesive. In various embodiments, the face shield comprises a porous, semi-porous, or non-porous material.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the devices of the present application, there are shown in the drawings preferred embodiments. It should be understood, however, that the application is not limited to the precise arrangements and instrumentalities shown. In the drawings.

DETAILED DESCRIPTION

Robotic surgery provides many advantages for the patient, including smaller incisions and fewer complications, and has become a common procedure throughout the world. However, existing robotic surgical systems pose particular problems for the surgeon, which are identified and solved by the present invention as detailed below.

Figure 1A:
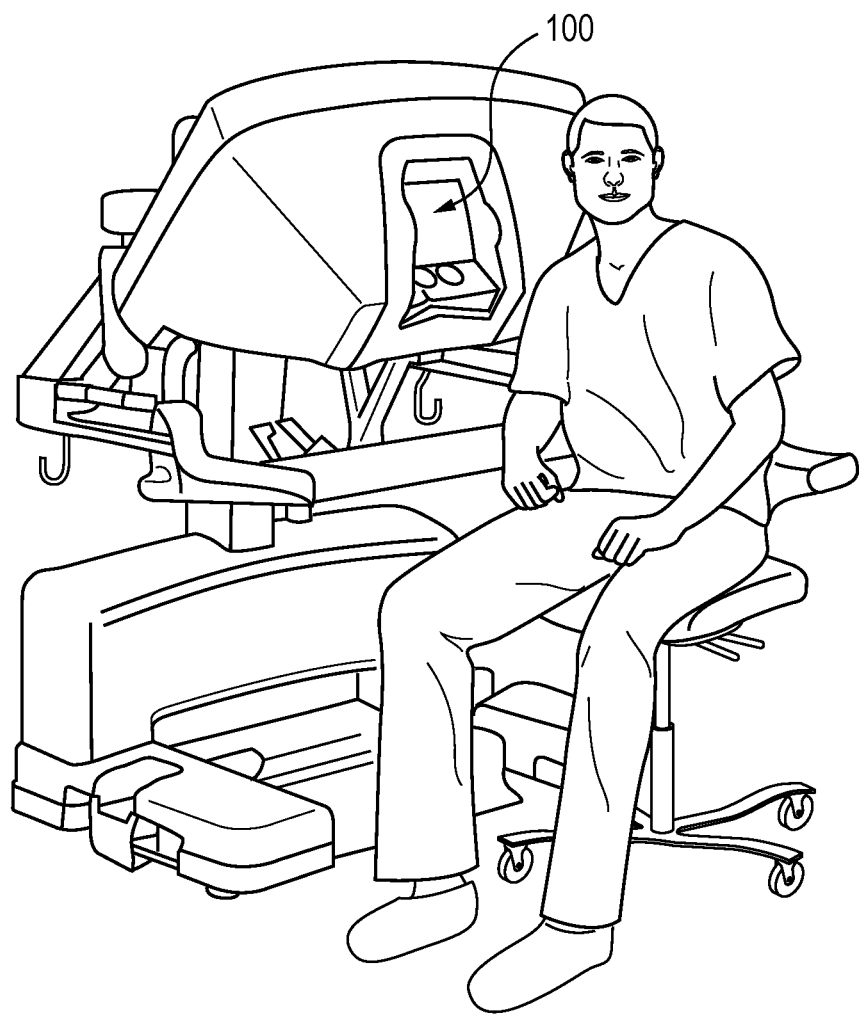
FIG. 1A shows a surgeon console of an exemplary robotic surgical system.
Figure 1B:
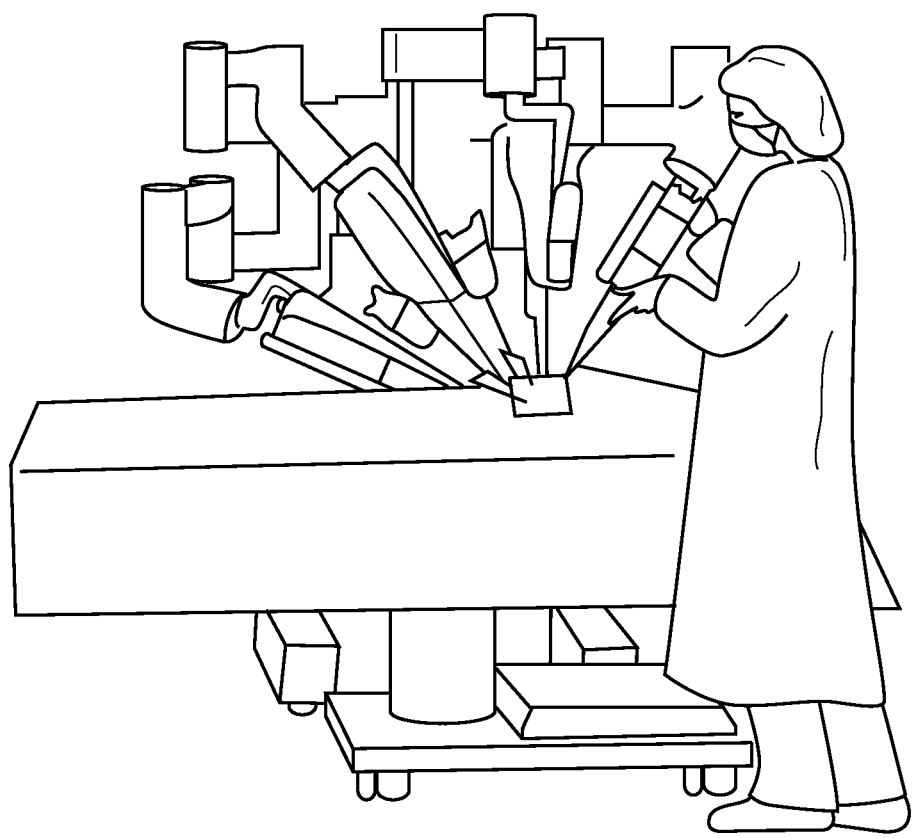
FIG. 1B shows a patient cart of an exemplary robotic surgical system.
Figure 1C:
FIG. 1C shows the surgeon console of FIG. 1A in use.

In a robotic surgical system such as that shown in FIGS. 1A-C, the surgeon sits at the surgeon console as shown in FIGS. 1A and 1C, and places his face onto a portion of the console 100 where the optics of the robot are situated. As shown in the close-up view of FIG. 2, the optical portion 200 of the robot comprises two ocular raised eyepieces 202 each having a glass portion 204 surrounded by a raised lip 206. The surgeon's forehead rests against a forehead rest 208. There is a notch 210 in the faceplate area (between the eyepieces) for the surgeon's nose to be positioned.

The present invention recognizes that the surgeon console is highly used and is not a sterile instrument. There are multiple users and substantial cross-contamination. The faceplate is in a semi-enclosed area on the console, with minimal ventilation. The eyepieces are open and are very difficult to clean due to their curves and shape and impossible to sterilize. The surgeon's eyes can physically touch portions of the eyepieces. There are gaps between portions of the faceplate area that are impossible to clean and impossible to sterilize. The spaces in the faceplate and the eyepieces also contain multiple viruses and bacteria, including but not limited to MRSA. Cleaning with alcohol before use is not sufficient. There is no protection for the surgeon, who is in high danger of eye infections and/or other infectious diseases when using the robotic surgeon console as shown in FIGS. 1A and 1C.

During surgery, the surgeon may wear a facemask, but the design of the facemask does not prohibit inhalation of bacteria or viruses that are on or around the faceplate.

The visualization through the eyepieces is such that the surgeon does not necessarily need to wear their corrective lenses if they have them, and surgeons typically do not use any eyewear or eye safety wear when utilizing the surgeon console, due to the small opening provided for the faceplate and the inability for face shields or safety goggles to comfortably fit in the allotted space. Thus, the surgeon is directly exposed to bacteria and viruses.

Another issue with sterility is that it is not uncommon for multiple surgeons to use the same surgeon console during the same procedure, with an inability to clean the optics at all.

For traditional open surgeries, various protective wear (e.g., gloves, gown, surgical mask, surgical cap, safety glasses, shoe covers) exists for the surgeon to wear to protect himself and/or the patient from fluids, infections, etc. However no such articles exist that are effective for use with robotic surgical systems.

The present invention provides, in various embodiments, an instrument shield comprising one or more eye shields and/or a face shield suitable for use with robotic surgical systems. Unlike traditional protective wear, the eye shield and the face shield of the present invention are constructed to fit onto/cover the contaminated instrument. Specifically, they are removably attached to the optical portion of the surgeon console; they are not worn by the surgeon. Viruses and bacteria on console are thus contained without restricting the surgeon, who is free to move around, step away from the console, etc. unencumbered by protective gear.

Figure 3:
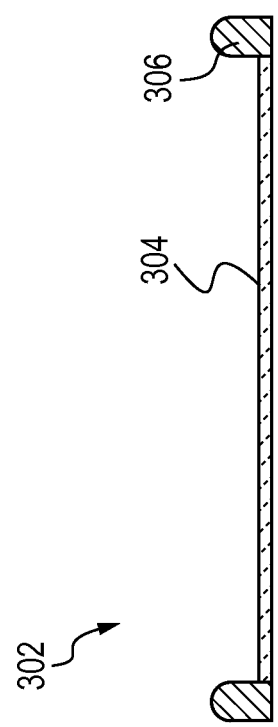
FIG. 3 shows a cross-sectional view of an eyepiece of the surgeon console of FIG. 2.

In some embodiments, the eye shield of the present invention is a transparent shield that fits over an eyepiece of the surgeon console. A cross-sectional view of an optical eyepiece on the surgeon console is shown in FIG. 3. The eyepiece 302 has a substantially flat glass portion 304 surrounded by a raised lip 306.

Figure 4B:
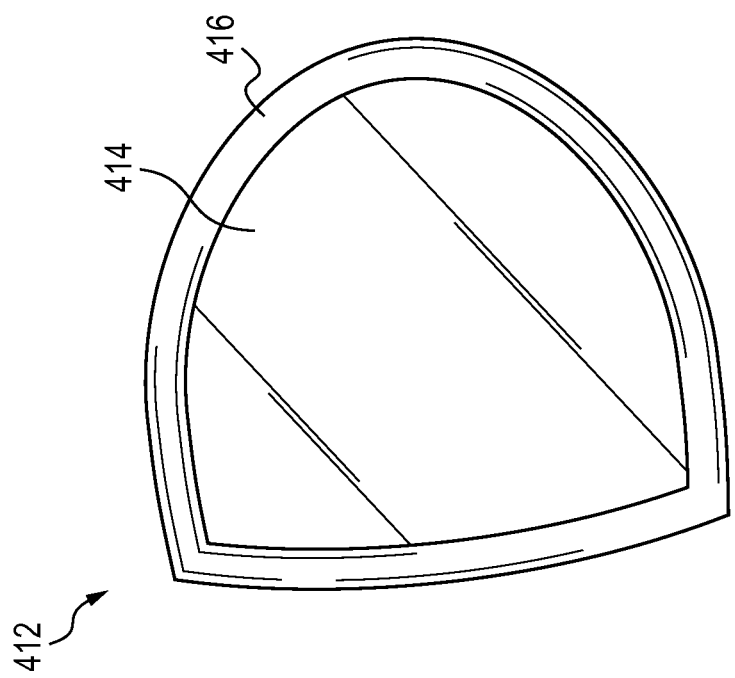
FIG. 4B shows a top view of the eye shield of FIG. 4A.
Figure 4A:
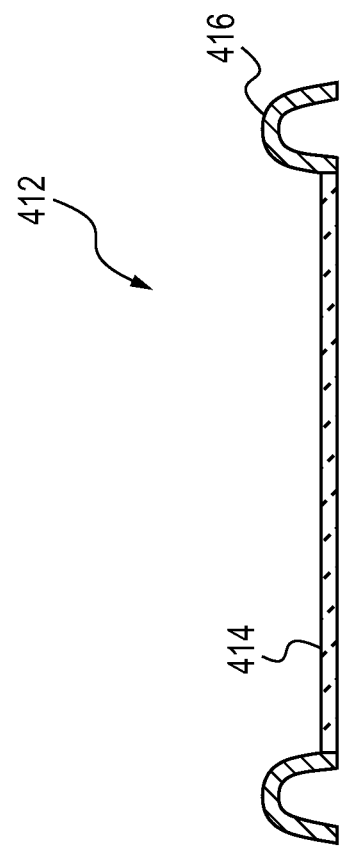
FIG. 4A shows a cross-sectional view of an eye shield, according to some embodiments of the invention.

In some embodiments, the eye shield of the present invention fits over the eyepiece and shields any direct contact between the console and the surgeon's eyes. As shown in FIG. 4, eye shield 412 includes a transparent lens 414 configured to cover glass portion 304 on the eyepiece. The shield fits over the eyepiece and can, for example, be held in place by friction in which there is a concave lip 416 on the eye shield that fits snugly over the convex lip 306 of the console's eyepiece. Utilizing this eye shield does not change the surgeon's visualization during a surgical procedure, but protects the surgeon from direct contact or close proximity of his eyes to the eyepieces of the robot.

The eye shields may be individual or attached to one another in a pair. Preferably, the portion 414 that covers the eyepiece glass 304 is clear plastic (e.g., hard optical grade plastic), so as not to alter the optics/3D image provided by the surgical system. The eye shield 412 can be formed to snap on to the eyepiece. For example, the eye shield may include a molded plastic or rubber rim 416 to attach by pressure to the eyepiece lip 306. In some embodiments, the eye shield can have an adhesive to help keep it in place.

In some embodiments, the instrument shield includes a face shield, either attached to the eye shields, or separately attached to the console. The face shield component of the instrument shield may cover the entire faceplate of the surgeon console, or just certain areas of the faceplate. The face shield can be made of can be made of a porous, semi-porous or non-porous material. Face shields can stay in position due to their attachment to the faceplate via the eye shields. Face shields can additionally or alternatively stay in position with the addition of adhesives.

Figure 5:
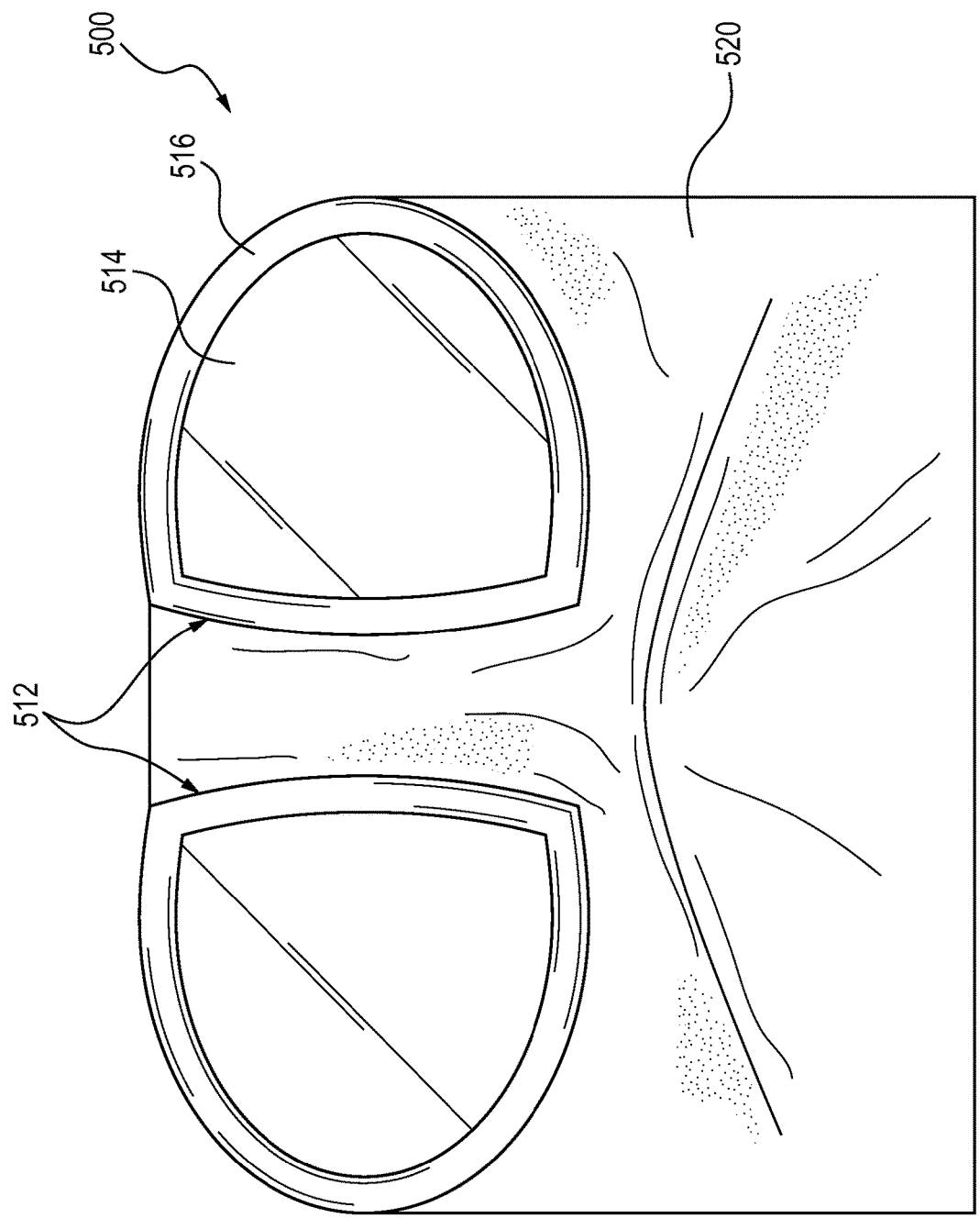
FIG. 5 shows an exemplary instrument shield, comprising two eye shields, each with transparent lens and concave lip, and a face shield attached thereto, according to some embodiments.

FIG. 5 shows an exemplary instrument shield 500, comprising two eye shields 512, each with transparent lens 514 and concave lip 516 to fit onto the corresponding eyepiece of the console, and a face shield 520 attached thereto. The eye shields and the face shield are preferably disposable.

Figure 2:
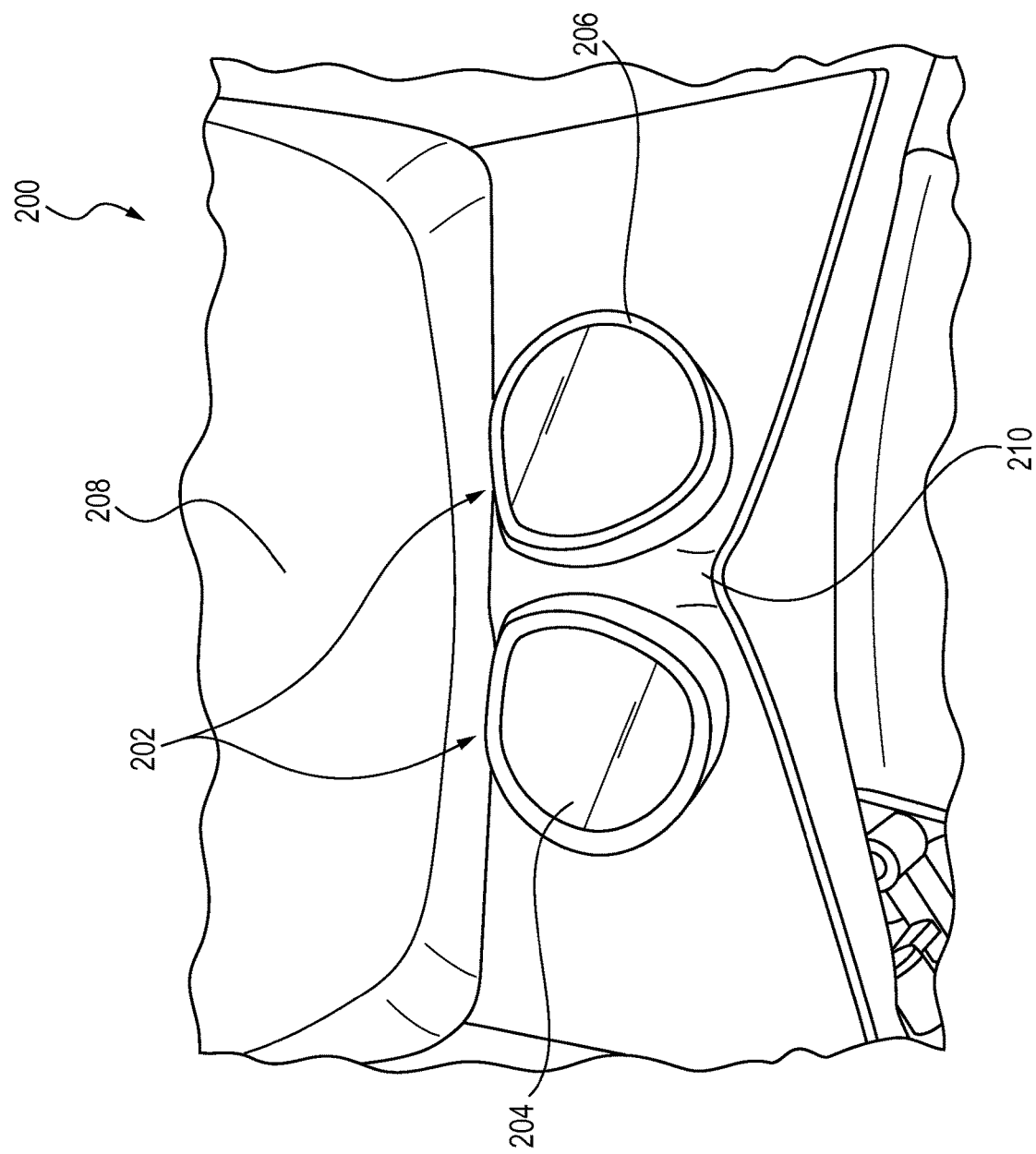
FIG. 2 shows a close-up view of the optical portion of the surgeon console of FIG. 1A.
Figure 6:
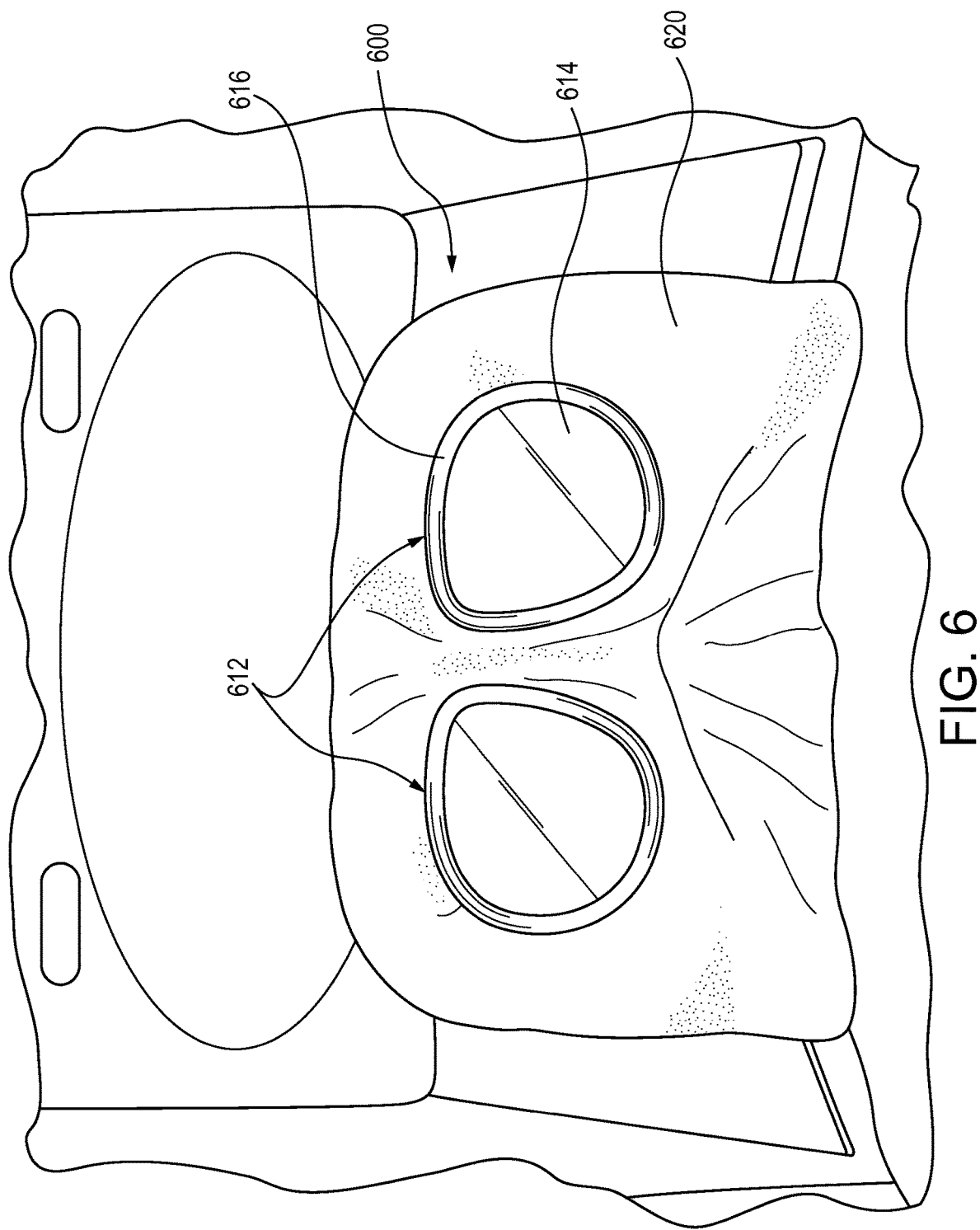
FIG. 6 shows a schematic illustrating the placement of an exemplary instrument shield on the surgeon console of FIG. 2, according to some embodiments.

FIG. 6 shows a schematic illustrating the placement of an exemplary instrument shield 600 on the surgeon console of FIG. 2, according to some embodiments. Each of the two eye shields 612 include a transparent lens 614 covering glass 204 of the console eyepiece, and a molded portion 616 configured to fit onto the lip 206 surrounding each eyepiece. Face shield 620 (shown here attached to eye shields 612) covers a portion of the faceplate of the surgeon console, including the nose indention 210 and part of the forehead rest 208.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. An instrument shield for a surgeon console of a robotic surgical system, comprising:
   first and second eye shields configured to be removably attached to respective eyepieces of the console;
   wherein each of the first and second eye shields includes an outer lip defining an integral perimeter groove to releasably engage the first and second eye shields with the respective eyepieces of the console; and
   a face shield is configured to be removably and separately attached to the console and to stay in position due to its attachment to a faceplate of the robotic surgical system via the eye shields.

2. The instrument shield of claim 1, wherein the first and second eye shields include clear plastic.

3. The instrument shield of claim 1, wherein the outer lip includes a molded plastic or rubber rim.

4. The instrument shield of claim 1, wherein the face shield is removably attached to the console with adhesive.

5. The instrument shield of claim 1, wherein the face shield includes a porous, semi-porous, or non-porous material.

6. The instrument shield of claim 1, wherein the first and second eye shields are configured to snap on to the respective eye pieces of the console.

* * * * *